US010253378B2

(12) United States Patent
Yang et al.

(10) Patent No.: US 10,253,378 B2
(45) Date of Patent: Apr. 9, 2019

(54) QUANTITATIVE ANALYSIS METHOD USING MICROORGANISM 16S RDNA GENE HAVING SINGLE NUCLEOTIDE POLYMORPHISM

(71) Applicant: KOREA RESEARCH INSTITUTE OF STANDARDS AND SCIENCE, Daejeon (KR)

(72) Inventors: Inchul Yang, Daejeon (KR); Hannah Yu, Daejeon (KR); Hyo-jin Yang, Daejeon (KR); Sook-Kyung Kim, Daejeon (KR); Sang-Ryoul Park, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 178 days.

(21) Appl. No.: 15/037,311

(22) PCT Filed: Nov. 18, 2014

(86) PCT No.: PCT/KR2014/011040
§ 371 (c)(1),
(2) Date: May 17, 2016

(87) PCT Pub. No.: WO2015/076542
PCT Pub. Date: May 28, 2015

(65) Prior Publication Data
US 2016/0376638 A1    Dec. 29, 2016

(30) Foreign Application Priority Data

Nov. 19, 2013    (KR) .................. 10-2013-0140292

(51) Int. Cl.
*C12Q 1/68*    (2018.01)
*C12Q 1/689*    (2018.01)

(52) U.S. Cl.
CPC ....... *C12Q 1/689* (2013.01); *C12Q 2600/156* (2013.01); *C12Q 2600/16* (2013.01)

(58) Field of Classification Search
None
See application file for complete search history.

(56) References Cited

FOREIGN PATENT DOCUMENTS

| EP | 1570086 B1 | 2/2013 |
|---|---|---|
| KR | 20110066018 A | 6/2011 |

OTHER PUBLICATIONS

Blok et al. (Biotechniques, 1997, 22:700-704).*
Li et al. (Plant Disease, 2007, vol. 91, No. 1, p. 51-58) (Year: 2007).*

(Continued)

*Primary Examiner* — Stephanie K Mummert
(74) *Attorney, Agent, or Firm* — McCoy Russell LLP (57) ABSTRACT

The present invention relates to utilization of an artificially synthesized nucleic acid, and more particularly, to a quantitative analysis method capable of quantitatively adjusting gene-based microbial community analysis results by preparing a microorganism 16S rDNA gene, which has a single nucleotide polymorphism (SNP) at a particular location so as to be differentiated from a gene of a target microorganism on the nucleotide sequence, and then using the microorganism 16S rDNA gene as an internal standard material which is quantifiable through nucleotide sequencing.

1 Claim, 4 Drawing Sheets

Specification includes a Sequence Listing.

(56) References Cited

OTHER PUBLICATIONS

Tsoloaki et al. (J Clin Microbiol, 2005, p. 3185-3191) (Year: 2005).*
Schloss et al. (PloS Computational Biology, 2010, 6(7):1-16) (Year: 2010).*
Hoorfar et al. (J of Clin Microbiol, 2004, 42(5):1863-1868) (Year: 2004).*
Block, H. et al., "Quantitative analysis of 16S rDNA using competitive PCR and the QPCR System 5000," BioTechniques, vol. 22, No. 4, Apr. 1997, 4 pages.
Schabereiter-Gurtner, C. et al., "16S rDNA-Based Identification of Bacteria from Conjunctival Swabs by PCR and DGGE Fingerprinting," Investigative Ophthalmology & Visual Science, vol. 42, No. 6, May 2001, 8 pages.
Yohda, M. et al., "Quantitative discrimination of 16 S rRNA genes of Dehalococcoides species by MagSNiPer, a quantitative single-nucleotide-polymorphism genotyping method," Biotechnology and Applied Biochemistry, vol. 51, Part 2, Oct. 2008, 7 pages.
ISA Korean Intellectual Property Office, International Search Report Issued in Application No. PCT/KR2014/011040, dated Feb. 15, 2016, WIPO, 4 pages.

* cited by examiner

SEQUENCE LISTING

<160> NUMBER OF SEQ ID NOS: 7

<210> SEQ ID NO 1
<211> LENGTH: 1534
<212> TYPE: DNA
<213> ORGANISM: Escherichia coli

<400> SEQUENCE: 1

```
agagtttgat catggctcag attgaacgct ggcggcaggc ctaacacatg caagtcgaac      60
ggtaacagaa agcagcttgc tgctttgctg acgagtggcg gacgggtgag taatgtctgg     120
gaaactgcct gatggagggg gatatctact ggaaacggta gctaataccg cataacgtcg     180
caagaccaaa gagggggacc ttcgggcctc ttgccatcgg atgtgcccag atgggattag     240
ctagcaggtg gggtaacggc tcacctaggc gacgatccct agctggtctg agaggatgac     300
cagccacact ggaactgaga cacggtccag actcctacgg gaggcagcag tggggaatat     360
tgcacaatgg gcgcaagcct gatgcagcca tgccgcgtgt atgaagaagg ccttcgggtt     420
gtacagtact ttcagcgggg aggaagggag taaagttaat acctttgctc attgacgtta     480
cccgcagaag aagcaccggc taactccgtg ccagcagccg cggtaatacg gagggtgcaa     540
gcgttaatcg gaattactgg gcgtaaagcg cacgcaggcg gtttgttaag tcagatgtga     600
aatccccggg ctcaacctgg gaactgcatc tgatactggc aagcttgagt ctcgtagagg     660
ggggtagaat accaggtgta gcggtgaaat gcgtagagat ctggaggaat accggtggcg     720
aaggcggccc cctggacgaa gactgacgct caggtgcgaa agcgtgggga gcaaacagga     780
ttagataccc tggtagtcca cgccgtaaac gatgtcgact tggaggttgt gcccttgagg     840
```

```
cgtggcttcc ggagctaacg cgttatgtcg accgcctggg gagtacggcc gcaaggttaa      900
aactcaaatg aattgacggg ggcccgcaca agcggtggag catgtggttt aattcgatgc      960
aacgcgaaga accttacctg gtcttgacgt ccacggaagt tttcagagat gagaatgtgc     1020
cttcgggaac cgtgagacag gtgctgcatg gctgtcgtca gctcgtgttg tgaaatgttg     1080
ggttaagtcc cgcaacgagc gcaaccctta tcctttgttg caagcggtcc ggccgggaac     1140
tcaaaggaga ctgccagtga taaactggag gaaggtgggg atgacgtcaa gtcatcatgg     1200
cccttacgac cagggctaca cacgtgctac aatggcgcat acaaagagaa gcgacctctc     1260
gagagcaagc ggacctcata aagtgcgtcg tagtccggat tggagtctgc aactcgactc     1320
catgaagtcg gaatcgctag taatcgtgga tcagaatgcc acggtgaata cgttcccggg     1380
ccttgtacac accgcccgtc acaccatggg agtgggttgc aaaagaagta ggtagcttaa     1440
gcttcgggag ggcgcttacc actttgtgat tcatgactgg ggtgaagtcg taacaaggta     1500
accgtagggg aacctgcggt tggatcacct cctt                                 1534

<210> SEQ ID NO 2
<211> LENGTH: 1554
<212> TYPE: DNA
<213> ORGANISM: Bacillus cereus

<400> SEQUENCE: 2
ctttattgga gagtttgatc ctggctcagg atgaacgctg gcggcgtgcc taatacatgc       60
aagtcgagcg aatggattaa gagcttgctc ttatgaagtt agcggcggac gggtgagtaa      120
cacgtgggta acctgcccat aagactggga tatctccggg aaaccggggc taataccgga      180
taacattttg aaccgcatgg ttcgaaattg aaaggcggct tcggctgtca cttatggatg      240
gacccgcgtc gcattagcta gctggtgagg taacggctca ccaaggcaac gatgcgtagc      300
cgacctgaga gggtgatcgg ccacactggg actgagacac ggcccagact cctacgggag      360
gcagcagtag ggaatcttcc gcaatggacg aaagtctgac ggagcaacgc cgcgtgagtg      420
atgaaggctt tcgggtcgta caactctgtt gttagggaag aacaagtgct agttgaataa      480
gctggcacct tgacggtacc taaccagaaa gccacggcta actacgtgcc agcagccgcg      540
gtaatacgta ggtggcaagc gttatccgga attattgggc gtaaagcgcg cgcaggtggt      600
ttcttaagtc tgatgtgaaa gcccacggct caaccgtgga gggtcattgg aaactgggag      660
acttgagtgc agaagaggaa agtggaatac catgtgtagc ggtgaaatgc gtagagatat      720
ggaggaacac cagtggcgaa ggcgactttc tggtctgtaa ctgacactga ggcgcgaaag      780
cgtggggagc aaacaggatt agataccctg gtagtccacg ccgtaaacga tgagtgctaa      840
gtgttagagg gtttccgccc tttagtgctg aagttaacgc attatgcact ccgcctgggg      900
agtacggccg caaggctgaa actcaaagga attgacgggg gcccgcacaa gcggtggagc      960
atgtggttta attcgaagca acgcgaagaa ccttaccagg tcttgacgtc tctgacaac     1020 cctagagata gggcttctcc ttcgggagca gagtgacagg tggtgcatgg ttgtcgtcag     1080
ctcgtgtcgt gagatgttgg gttaagtccc gcaacgagcg caacccttga tcttagttgc     1140
aatcattcag ttgggcactc taaggtgact gccggtgaca accgaggaa ggtggggat     1200 gacgtcaaat catcatgccc cttatgacct gggctacaca cgtgctacaa tggacggtac     1260
aaagagctgc aagacctcga ggtggagcta atctcataaa accgttctca gttcggattg     1320
taggctgcaa ctcgcctaca tgaagctgga atcgctagta atcgcggatc agcatgccgc     1380
```

| | |
|---|---|
| ggtgaatacg ttcccgggcc ttgtacacac cgcccgtcac accacgagag tttgtaacac | 1440 |
| ccgaagtcgg tggggtaagc ttttggagcc agccgcctaa ggtgggacag atgattgggg | 1500 |
| tgaagtcgta acaaggtagc cgtatcggaa ggtgcggctg gatcacctcc tttc | 1554 |

<210> SEQ ID NO 3
<211> LENGTH: 1550
<212> TYPE: DNA
<213> ORGANISM: Listeria monocytogenes

<400> SEQUENCE: 3

| | |
|---|---|
| ttaaagagag tttgatcctg gctcaggacg aacgctggcg gcgtgcctaa tacatgcaag | 60 |
| tcgaacgaac ggaggaagag cttgctcttc caaagttagt ggcggacggg tgagtaacac | 120 |
| gtgggcaacc tgcctgtaag ttggggatat ctccggaaaa ccggggctaa taccgaatga | 180 |
| taaagtttgg cgcatgccac gcttttgaaa gatggtttcg gctatcgctt acagatgggc | 240 |
| ccgcggtgca ttagctagct ggtagggtaa tggcctacca aggcaacgat gcatagccga | 300 |
| cctgagaggg tgatcggcca cactgggact gagacacggc ccagactcct acgggaggca | 360 |
| gcagtaggga tcttccgca atggacgaaa gtctgacgga gcaacgccgc gtgtatgaag | 420 |
| aaggttttcg gatcgtacag tactgttgtt agagaagaac aaggataaga gtaactgctt | 480 |
| gtcccttgac ggtatctaac cagaaagcca cggctaacta cgtgccagca gccgcggtaa | 540 |
| tacgtaggtg gcaagcgttg tccggattta ttgggcgtaa agcgcgcgca ggcggtcttt | 600 |
| taagtctgat gtgaaagccc ccggcttaac cggggagggt cattggaaac tggaagactg | 660 |
| gagtgcagaa gaggagagtg gaataccacg tgtagcggtg aaatgcgtag atatgtggag | 720 |
| gaacaccagt ggcgaaggcg actctctggt ctgtaactga cgctgaggcg cgaaagcgtg | 780 |
| gggagcaaac aggattagat accctggtag tccacgccgt aaacgatgag tgctaagtgt | 840 |
| taggggtttt ccgccccta gtgctgcagc taacgcatta tgcactccgc ctggggagta | 900 |
| cgaccgcaag gttgaaactc aaaggaattg acggggccc gcacaagcgg tggagcatgt | 960 |
| ggtttaattc gaagcaacgc gaagaacctt accaggtctt gacgtccttt gaccactctg | 1020 |
| gagacagagc tttcccttcg gggacaaagt gacaggtggt gcatggttgt cgtcagctcg | 1080 |
| tgtcgtgaga tgttgggtta agtcccgcaa cgagcgcaac ccttgatttt agttgcaagc | 1140 |
| atttagttgg gcactctaaa gtgactgccg gtgcaagccg gaggaaggtg gggatgacgt | 1200 |
| caaatcatca tgccccttat gacctgggct acacacgtgc tacaatggat agtacaaagg | 1260 |
| gtcgcgaagc ctcgaggtgg agctaatccc ataaaactat tctcagttcg gattgtaggc | 1320 |
| tgcaactcgc ctacatgaag ccggaatcgc tagtaatcgt ggatcagcat gccacggtga | 1380 |
| atacgttccc gggccttgta cacaccgccc gtcacaccac gagagtttgt aacacccgaa | 1440 |
| gtcggtaggg taagctttat ggagccagcc gccgaaggtg ggacagataa ttggggtgaa | 1500 |
| gtcgtaacaa ggtagccgta tcggaaggtg cggctggatc acctcctttc | 1550 |

<210> SEQ ID NO 4
<211> LENGTH: 1554
<212> TYPE: DNA
<213> ORGANISM: Staphylococcus aureus

<400> SEQUENCE: 4

| | |
|---|---|
| ttttatggag agtttgatcc tggctcagga tgaacgctgg cggcgtgcct aatacatgca | 60 |
| agtcgagcga acggacgaga agcttgcttc tctgatgtta gcggcggacg ggtgagtaac | 120 |
| acgtggataa cctacctata agactgggat atcttcggga aaccggagct aataccggat | 180 |

```
aatattttga accgcatggt tcaaaagtga agacggtct tgctgtcact tatagatgga      240
tccgcgctgc attagctagc tggtaaggta acggcttacc aaggcaacga tgcatagccg      300
acctgagagg gtgatcggcc acactggaac tgagacacgg tccagactcc tacgggaggc      360
agcagtaggg aatcttccgc aatgggcgaa agcctgacgg agcaacgccg cgtgagtgat      420
gaaggtcttc ggatcgtaca actctgttat tagggaagaa catatgtgta agtaactgtg      480
cacatcttga cggtacctaa tcagaaagcc acggctaact acgtgccagc agccgcggta      540
atacgtaggt ggcaagcgtt atccggaatt attgggcgta aagcgcgcgt aggcggtttt      600
ttaagtctga tgtgaaagcc cacggctcaa ccgtggaggg tcattggaaa ctggaaaact      660
tgagtgcaga agaggaaagt ggaataccat gtgtagcggt gaaatgcgca gagatatgga      720
ggaacaccag tggcgaaggc gactttctgg tctgtaactg acgctgatgt gcgaaagcgt      780
ggggatcaaa caggattaga taccctggta gtccacgccg taaacgatga gtgctaagtg      840 ttaggggggtt tccgcccctt agtgctgcag ctaacgcatt atgcactccg cctggggagt      900
acgaccgcaa ggttgaaact caaaggaatt gacggggacc cgcacaagcg gtggagcatg      960
tggtttaatt cgaagcaacg cgaagaacct taccaaatct tgacgtcctt tgacaactct     1020
agagatagag ccttcccctt cggggggacaa agtgacaggt ggtgcatggt tgtcgtcagc     1080
tcgtgtcgtg agatgttggg ttaagtcccg caacgagcgc aacccttaag cttagttgca     1140
atcattaagt tgggcactct aagttgactg ccggtgacaa accggaggaa ggtggggatg     1200
acgtcaaatc atcatgcccc ttatgatttg ggctacacac gtgctacaat ggacaataca     1260
aagggcagcg aaacctcgag gtcaagcaaa tcccataaag ttgttctcag ttcggattgt     1320
agtctgcaac tcgactacat gaagctgaa tcgctagtaa tcgtagatca gcatgctacg     1380
gtgaatacgt tcccgggtct tgtacacacc gcccgtcaca ccacgagagt ttgtaacacc     1440
cgaagccggt ggagtaagct tttaggagct agccgtcgaa ggtgggacaa atgattgggg     1500
tgaagtcgta acaaggtagc cgtatcggaa ggtgcggctg gatcacctcc tttc         1554
```

<210> SEQ ID NO 5
<211> LENGTH: 17
<212> TYPE: DNA
<213> ORGANISM: Artificial Sequence
<220> FEATURE:
<223> OTHER INFORMATION: 334F forward primer

<400> SEQUENCE: 5
cctacgggag gcagcag                                                    17

<210> SEQ ID NO 6
<211> LENGTH: 17
<212> TYPE: DNA
<213> ORGANISM: Artificial Sequence
<220> FEATURE:
<223> OTHER INFORMATION: 511F forward primer

<400> SEQUENCE: 6
cctacgggag gcagcag                                                    17

<210> SEQ ID NO 7
<211> LENGTH: 21

```
<212> TYPE: DNA
<213> ORGANISM: Artificial Sequence
<220> FEATURE:
<223> OTHER INFORMATION: 798R reverse primer

<400> SEQUENCE: 7
gactaccagg gtatctaatc c                                              21
```

QUANTITATIVE ANALYSIS METHOD USING MICROORGANISM 16S RDNA GENE HAVING SINGLE NUCLEOTIDE POLYMORPHISM

CROSS REFERENCE TO RELATED APPLICATIONS

The present application is a U.S. National Phase of International Patent Application Serial No. PCT/KR2014/011040, entitled "QUANTITATIVE ANALYSIS METHOD USING MICROORGANISM 16S RDNA GENE HAVING SINGLE NUCLEOTIDE POLYMORPHISM," filed on Nov. 18, 2014, which claims priority to Korean Patent Application No. 10-2013-0140292, entitled "QUANTITATIVE ANALYSIS METHOD USING MICROORGANISM 16S RDNA GENE HAVING SINGLE NUCLEOTIDE POLYMORPHISM," filed on Nov. 19, 2013, the entire contents of each of which are hereby incorporated by reference for all purposes.

INCORPORATION BY REFERENCE OF ELECTRONICALLY SUBMITTED MATERIAL

Incorporated by reference in its entirety herein is a computer-readable nucleotide sequence listing submitted herewith and identified as follows: 9,041 bytes ASCII (Text) file named "Substitute Sequence_Listing_PLS16310PCTUS," created Aug. 29, 2016.

TECHNICAL FIELD

The present invention relates to utilization of an artificially synthesized nucleic acid, and more particularly, to a quantitative analysis method capable of quantitatively adjusting gene-based microbial community analysis results by preparing a microorganism 16S ribosomal DNA (rDNA) gene, which has a single nucleotide polymorphism (SNP) at a particular location so as to be differentiated from a gene of a target microorganism on the nucleotide sequence, and then using the microorganism 16S rDNA gene as a competitor or an internal standard material which is quantifiable through nucleotide sequencing.

BACKGROUND ART

Microbial community analysis is a technique widely used in order to detect a harmful microorganism existing in an environment, food, and human body. Particularly, in a case of utilizing a 16S rDNA analysis method and a multiple locus strain typing (MLST) method, which are based on microorganism gene amplification through polymerase chain reaction (PCR), in the microbial community analysis, it is possible to obtain more detailed information on the kind of microorganism derived from an environment, food, animals, and human bodies, whether or not the microorganism is mutated, resistance of the microorganism against antibiotics, and the like through high-sensitivity and high-precision genetic analysis. Recently, a technology capable of rapidly performing microbial community analysis on several hundreds of unknown microorganisms collected in various environments using next generation sequencing (NGS) has been known. The microbial community analysis based on gene analysis may have an advantage in that various microorganisms may be simultaneously detected within a short analysis time, but has a limitation in quantitative microbial community analysis. The limitation of gene-based microbial community analysis may be caused by differences in genome extraction and amplification efficiency depending on the microorganism. Particularly, in microbial community analysis based on microorganism 16S rDNA gene amplification, since 16S rDNA gene is amplified using a degenerate primer in order to simultaneously amplify as many kinds of microorganism genes as possible, bias in amplification of genes may be increased depending on the microorganism. The bias in amplification of genes is more clearly observed in a case of precisely analyzing an origin of the gene through NGS. Bias caused by a PCR amplification process is observed in microbial community analysis results through NGS, and it is known that the gene amplification bias is affected by an amplification location, a nucleotide sequence of the primer, or the like.

Therefore, in order to improve accuracy of gene-based quantitative microbial community analysis, a novel technology capable of overcoming the bias in amplification of genes attendant on PCR has been urgently demanded.

DISCLOSURE

Technical Problem

An object of the present invention is to provide a quantitative analysis method capable of quantitatively adjusting bias in amplification of a 16S rDNA gene, which is different depending on the kind of microorganism, by preparing a DNA in which a nucleotide sequence of an amplification target original gene (16S rDNA) is partially artificially substituted so as to have a single nucleotide polymorphism (SNP), and then using the prepared DNA as an internal standard material (SNP 16S DNA).

Technical Solution

In one general aspect, a gene-based quantitative microbial community analysis method of a community includes: a) preparing a single nucleotide polymorphism (SNP) 16S DNA of which a nucleotide sequence is partially substituted so as to have a single nucleotide polymorphism (SNP) with respect to of a 16S rDNA gene; b) adding the SNP 16S DNA to an analysis target sample to simultaneously amplify the added SNP 16S DNA and 16S rDNA; c) distinguishing the 16S rDNA and the SNP 16S DNA from each other through nucleotide sequencing of the materials amplified in step b) to quantify the 16S rDNA and the SNP 16S DNA; and d) dividing an amount of the 16S rDNA quantified in step c) by an amount of the SNP 16S DNA to adjust amplification efficiency of the 16S rDNA.

The SNP 16S DNAs prepared from 1 to 30 kinds of communities different from each other may be simultaneously added.

Although not limited, as the 16S rDNA gene in step a), a cDNA synthesized from an RNA by a reverse transcription reaction may be used.

Although not limited, preferably, the community may be genomes derived from microorganisms or eukaryotes. Although not limited, the microorganism may be one or more selected among *Escherichia coli, Bacillus cereus, Listeria monocytogenes*, and *Staphylococcus aureus*, and the eukaryotes may be one or more organism selected from animals, plants, and fungi.

Figure 1:
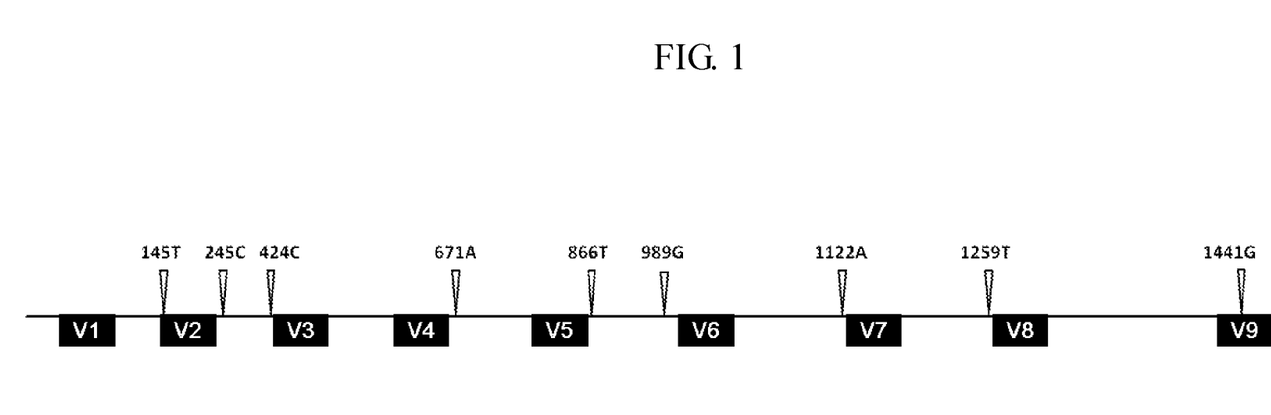
FIG. 1 illustrates a schematic structure of a microorganism SNP 16S DNA and locations of 9 single nucleotide polymorphisms. V1 to V9 are variable regions used to classify the microorganism.
Figure 2:
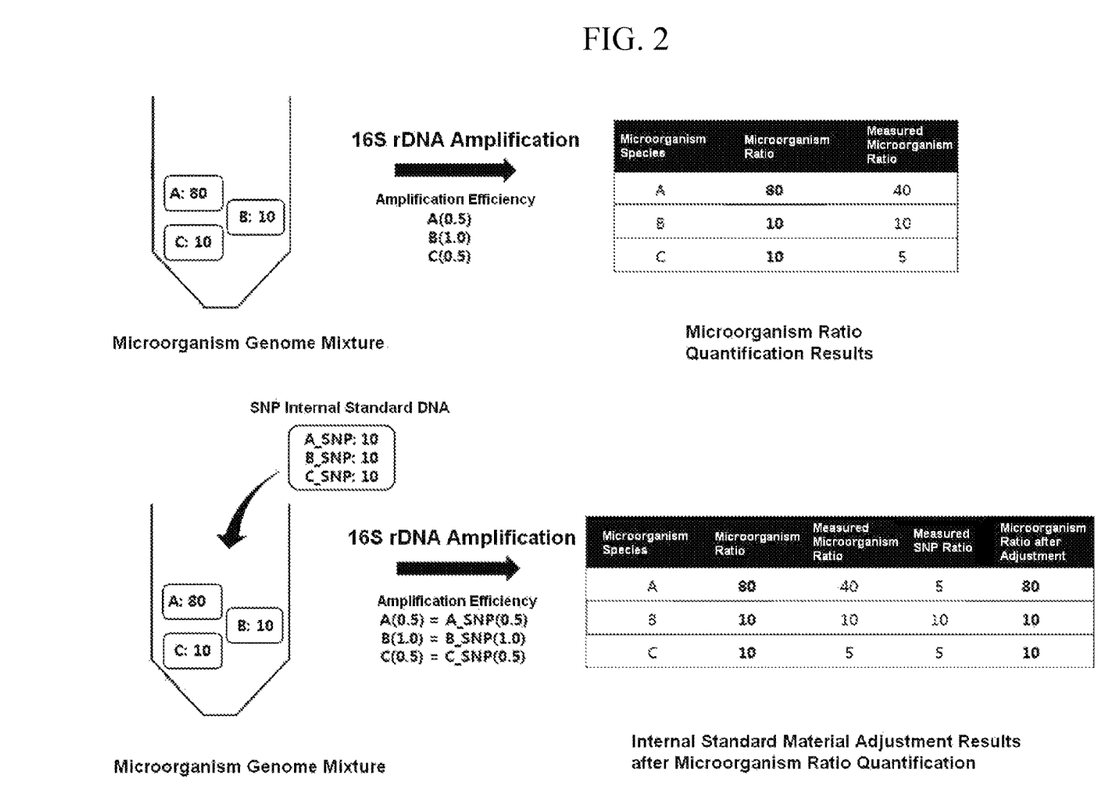
FIG. 2 illustrates a method of adjusting amplification efficiency of a 16S rDNA using the SNP 16S DNA as an internal standard material.
Figure 3:
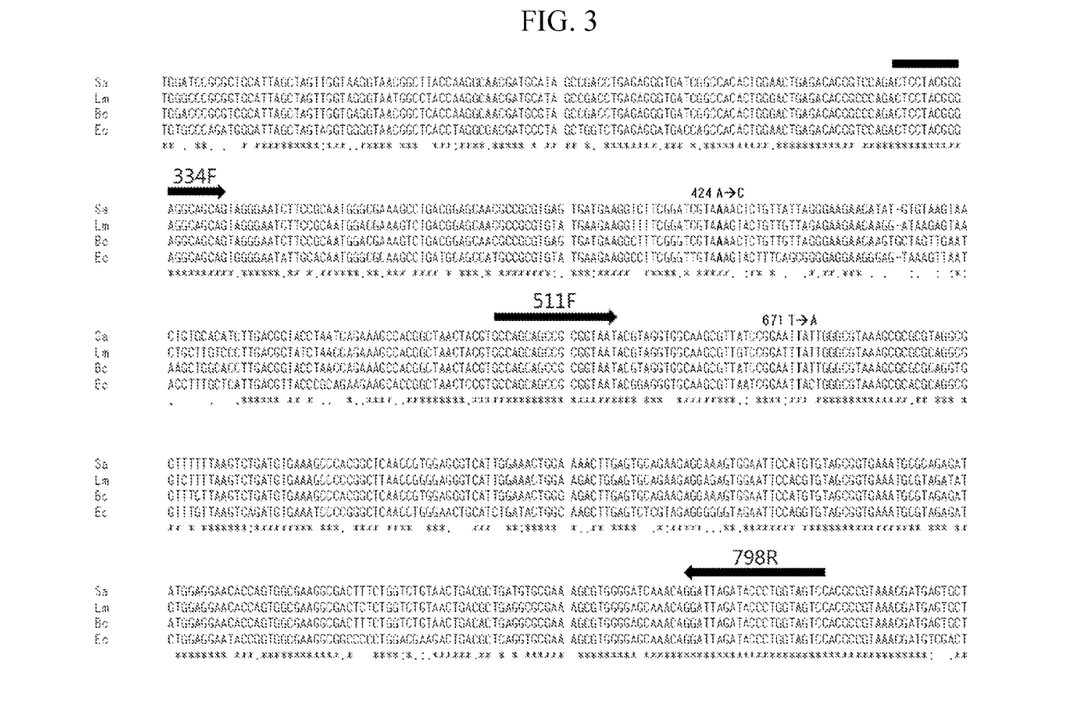
FIG. 3 illustrates locations of a primer used to amplify a 16S rDNA and a single nucleotide polymorphism included in an amplification product.

The SNP 16S DNA artificially prepared so as to have the single nucleotide polymorphism (SNP) may have a single nucleotide polymorphism at each nucleotide sequence of 150 bp on average at locations which are not amplification primer binding sites (FIG. 1). The prepared SNP 16S DNA may have a nucleotide sequence homology of about 99% with the 16S rDNA. In particular, since the nucleotide sequence thereof is completely the same as that of the 16S rDNA at an amplification primer binding site, amplification efficiency of the SNP 16S DNA may be the same as that of an original gene in a gene amplification process. A ratio between the amounts of the 16S rDNA and SNP 16S DNA may be calculated by sequencing 16S rDNA amplified as described above, and it is possible to overcome bias in quantification of the microorganism due to bias in amplification efficiency by applying a value obtained by dividing an amount of the 16S rDNA amplified in a specific microorganism by an amount of the SNP 16S DNA.

Advantageous Effects

According to the present invention, at the time of quantitatively analyzing a microbial community through gene analysis, accuracy of the analysis may be improved by adjusting amplification efficiency of genes which is different depending on the microorganism. Therefore, effects of a microorganism in various environments, factors of causing diseases, efficacy of an antibiotic, and the like, may be precisely analyzed by providing accurate quantification information on a microbial community existing in human bodies, foods, or environments. Further, the present invention may be utilized to effectively correspond to a pathogenic microorganism. In addition, the present invention may also be used to improve medical and industrial utility of the microorganism.

BEST MODE

Hereinafter, the present invention will be described in detail with reference to Examples. However, the Examples have been disclosed for illustrative purposes, but the scopes of the present invention are not limited thereby.

(Example 1) Preparation of SNP 16S DNA

SNP 16S DNAs were prepared with respect to *Escherichia coli, Bacillus cereus, Listeria monocytogenes,* and *Staphylococcus aureus.* 16S rDNA nucleotide sequences of the four kinds of microorganisms were obtained from NCBI GenBank, and aligned using a ClustalW-based multiple sequence alignment program (http://www.genome.jp/tools/clustalw). The nucleotide sequence was substituted so as to have nine single nucleotide polymorphisms scattered at locations which are close to variable regions and at which an interspecies nucleotide sequence homology is excellent on the aligned nucleotide sequence (FIG. 1). Four kinds of SNP 16S DNAs having nine single nucleotide polymorphisms as compared to the 16S rDNAs of the four microorganisms were prepared (Bioneer, Korea), respectively, and inserted into a plasmid vector (pGEM-B1™, Bioneer). Nucleotide sequences of the prepared four kinds of SNP 16S DNAs were confirmed using a 3730 DNA analyzer (Life Technologies, Carlsbad, Calif., USA).

A length of the SNP 16S DNA sequence with respect to *E. coli* (Ec_SNP) was 1534 bp (SEQ ID No. 1), a length of the SNP 16S DNA sequence with respect to *B. cereus* (BC_SNP) was 1554 bp (SEQ ID No. 2), a length of the SNP 16S DNA sequence with respect to *L. monocytogenes* (Lm_SNP) was 1550 bp (SEQ ID No. 3), and a length of the SNP 16S DNA sequence with respect to *S. aureus* (Sa_SNP) was 1554 bp (SEQ ID No. 4).

(Example 2) Gene-Based Quantitative Microbial Community Analysis Using SNP 16S DNA Genome Extraction and Quantification Genomes were extracted from *Escherichia coli* (KCTC 2571, ATCC 8739), *Bacillus cereus* (KCTC 1012, ATCC 11778), *Listeria monocytogenes* (KCTC 3710, ATCC 19115), and *Staphylococcus aureus* (KCTC 1916, ATCC 23832) using a GenElute™ Bacterial Genomic DNA kit (Sigma, St. Louis, USA). The extracted genomes were fragmented using a sonicator (Vibra Cell 500; Sonics, Newtown, USA) at 35% power so as to have a size of about 500 bp to 3 kb, and then quantified using PicoGreen assay (Life Technologies, Carlsbad, USA). Quantitative polymerase chain reaction (qPCR; SYBR premix EX Taq™; Takara, Otsu, Japan) was performed on the quantified genomic DNAs of four kinds of microorganisms using a forward primer 511F (5'-CCTACGGGAGGCAGCAG-3', SEQ ID No. 6) and a reverse primer 798R (5'-GACTACCAGGG-TATCTAATCC-3', SEQ ID No. 7).

Four kinds of genomes were mixed based on amounts of the genomes, and PCR was performed so that a final concentration of each of the 16S rDNAs was 200,000 copies/µL. After the SNP 16S DNA was quantified using PicoGreen Assay through the same procedure as described above, qPCR was performed so that a final concentration of each of the SNP 16S DNAs was 200,000 copies/µL. A template mixture was prepared by mixing the mixture of four kinds of genomes and a mixture of the SNP DNAs at a ratio of 1:1 so that a concentration of eight kinds of 16S DNAs was 100,000 copies/µL.

Amplification Efficiency of 16S rDNA and SNP 16S DNA

After PCR for amplifying 16S genes was performed on the template mixture in which the same amounts of 16S rDNA and SNP 16S DNA were mixed with each other, the PCR products were analyzed using a next generation sequencing instruments (Miseq™, Illumina, San Diego, USA). After an amplification reaction mixture to which the template mixture obtained by mixing the primer (500 nm) and 100,000 copies of each of the 16S DNAs with each other was added was prepared using qPCR, a standard amplification reaction was performed using a StepOne Plus™ apparatus (Life Technologies) in a final volume of 20 µL. As temperature cycling conditions, after initial denaturation at 95° C. for 5 minutes, a two-step cycling reaction (at 94° C. for 15 seconds and at 60° C. for 1 minute) was performed for 40 cycles. As a final reaction, an extension reaction was performed at 60° C. for 5 minutes, thereby completing the amplification reaction.

Amplification reactions were performed under a condition at which 1 mM EDTA, an amplification reaction inhibitor, was added, a condition at which 5% DMSO, an amplification reaction promoter, was added, a condition at which the number of cycles of the amplification reaction was decreased to 20 cycles, a 2N condition at which the number of arbitrary nucleotide sequence N existing in a nucleotide sequence of each of the primers was 2, and the like, respectively, in addition to the standard amplification reaction condition, thereby testing amplification efficiency of the 16S rDNA and the SNP 16S DNA. About 2 million nucleotide sequences analyzed by the next generation sequencing instruments were classified into database items having the highest similarity by comparing nucleotide sequence similarities thereof with respect to four kinds of 16S rDNA nucleotide sequences and four kinds of SNP 16S DNA nucleotide sequences depending on each of the microorganisms. In this case, data having nucleotide sequences different from those of the 16S rDNA and the SNP 16S DNA at an SNP site were excluded, and nucleotide sequences having similarity to two or more data bases were also excluded. The results were illustrated in Table 1.

TABLE 1

|  | Ec_g | Ec_SNP | Ec_g/ Ec_SNP | Bc_g | Bc_SNP | Bc_g/ Bc_SNP | Lm_g | Lm_SNP | LM_g/ Lm_SNP |
|---|---|---|---|---|---|---|---|---|---|
| Normal 1 | 6442 | 2553 | 2.52 | 7600 | 2851 | 2.67 | 4074 | 1775 | 2.30 |
| Normal 2 | 74562 | 32101 | 2.32 | 87619 | 32496 | 2.70 | 67207 | 29384 | 2.29 |
| DMSO | 15168 | 5875 | 2.58 | 13392 | 5336 | 2.51 | 8839 | 3375 | 2.62 |
| N2 | 119369 | 48095 | 2.48 | 129119 | 49882 | 2.59 | 89423 | 41451 | 2.16 |
| 20 cycle | 1922 | 671 | 2.86 | 2636 | 867 | 3.04 | 1476 | 623 | 2.37 |
| EDTA | 749 | 271 | 2.76 | 619 | 232 | 2.67 | 2242 | 1032 | 2.17 |

* Ec_g, Ec_SNP, Bc_g, Bc_SNP, Lm_g, and Lm_SNP illustrate read count values.

The results illustrated in Table 1 indicate that amplification efficiency of the 16S rDNA was different depending on amplification reaction conditions. For example, in the case of 16S rDNA (Ec_g) of *E. coli*, a nucleotide sequence frequency was changed from 749 to 119,369 depending on the amplification reaction conditions, which indicates an amplification rate of about 150 times. However, it was confirmed that since in the cases of the SNP 16S DNA (Ec_SNP), a similar amplification rate was maintained, a value of Ec_g/Ec_SNP was maintained at about 2.5 regardless of the amplification conditions.

Figure 4:
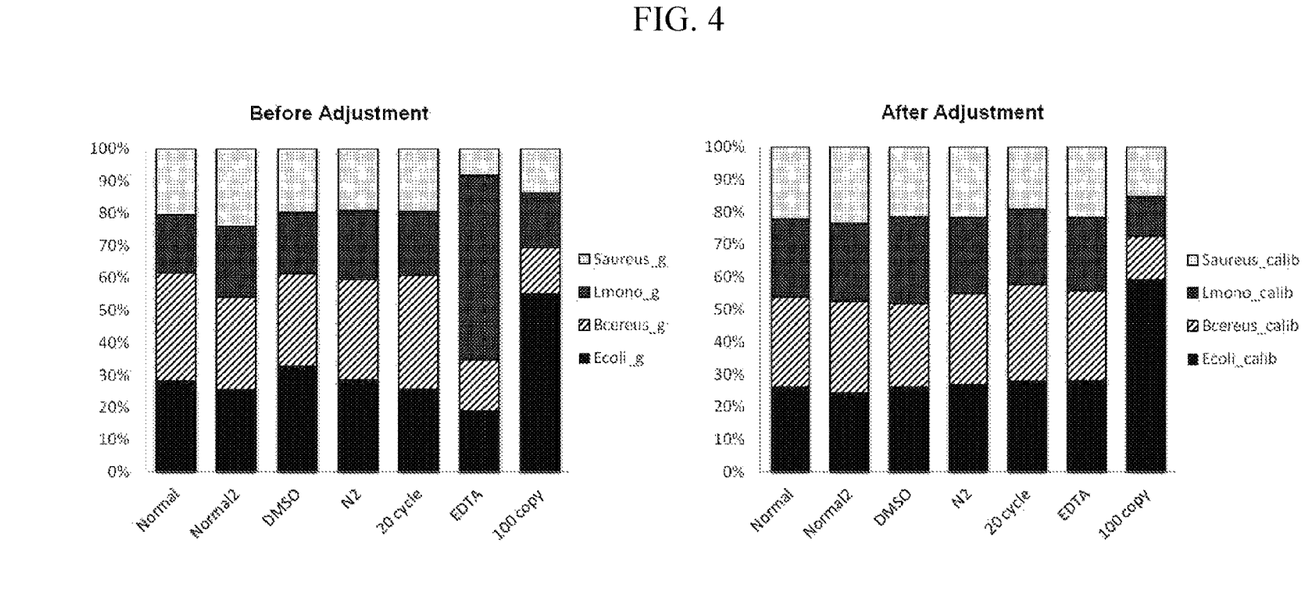
FIG. 4 is a graph illustrating adjustment of amplification efficiency of a 16S rDNA of each microorganism using a SNP 16S DNA as an internal standard material.

An amount of the genome of each of the microorganisms existing in the template mixture was quantitatively analyzed based on a 16S rDNA nucleotide sequence frequency of each of the microorganisms of which the amplification rate was adjusted, and the results were illustrated in FIG. 4. A mixing ratio of each of the microorganism genomes calculated after amplification adjustment, was close to 25%. Particularly, it was confirmed that adjustment by the SNP 16S DNA was appropriately operated even under the condition of 20 cycles or an unfriendly condition at which EDTA was added.

It was confirmed from the Examples that the SNP 16S DNA of each of the microorganisms had the same amplification efficiency as that of the 16S rDNA thereof under various gene amplification conditions, and it was found that accuracy of quantitative microbial community analysis result of which amplification efficiency was adjusted was significantly high, thereby completing the present invention.

[Sequence List Free Text]

SEQ ID No. 1 is a SNP 16S DNA prepared with respect to *Escherichia coli*.

SEQ ID No. 2 is a SNP 16S DNA prepared with respect to *Bacillus cereus*.

SEQ ID No. 3 is a SNP 16S DNA prepared with respect to *Listeria monocytogene*.

SEQ ID No. 4 is a SNP 16S DNA prepared with respect to *Staphylococcus aureus*.

SEQ ID No. 5 is a forward primer 334F for 16S DNA amplification.

SEQ ID No. 6 is a forward primer 511F for 16S DNA amplification.

SEQ ID No. 7 is a reverse primer 798R for 16S DNA amplification.

The invention claimed is:

1. A gene-based quantitative microbial community analysis method comprising:
   a) preparing a single nucleotide polymorphism (SNP) 16S DNA of which specific nucleotide sequences are substituted so as to have single nucleotide polymorphisms (SNP) with respect to of a natural microorganismal 16S rDNA gene,
   wherein the SNP 16S DNA has a single nucleotide polymorphisms scattered at locations close to the variable regions, V1~V9, and between variable region V1 and V9, wherein the SNP 16s DNAs prepared for 1 to 30 different microorganisms are simultaneously added, and wherein the microorganism includes one or more selected among *Escherichia coli*, *Bacillus cereus*, *Listeria monocytogenes*, and *Staphylococcus aureus*;
   b) adding the SNP 16S DNA to an analytical target sample to simultaneously amplify the added SNP 16S DNA together with the natural microorganismal 16S rDNA;
   c) distinguishing the natural microorganismal 16S rDNA and the added SNP 16S DNA from each other through nucleotide sequencing of the materials amplified in step b) to quantify the natural microorganismal 16S rDNA and the added SNP 16S DNA; and
   d) dividing an amount of the natural microorganismal 16S rDNA quantified in step c) by an amount of the added SNP 16S DNA to calibrate the amplification efficiency of the 16S rDNA.

* * * * *